(12) United States Patent
Desbrosses et al.

(10) Patent No.: US 11,883,363 B2
(45) Date of Patent: Jan. 30, 2024

(54) RECONSTITUTION SYSTEM TO ADMINISTER A DRUG VIA A HIGH VACUUM VIAL WITH INTEGRATED VENT CONDUIT

(71) Applicants: BAXTER INTERNATIONAL INC., Deerfield, IL (US); BAXTER HEALTHCARE SA, Glattpark (CH)

(72) Inventors: Freddy Desbrosses, Thuin (BE); Pierpaolo Padula, Etterbeek (BE); Marjorie Desriaux, Etterbeeck (BE); Yannis Abdessalem, Ixelles (BE); Diego Santo-Domingo Porqueras, Ixelles (BE)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 0 days.

(21) Appl. No.: 17/966,963

(22) Filed: Oct. 17, 2022

(65) Prior Publication Data

US 2023/0043283 A1 Feb. 9, 2023

Related U.S. Application Data

(63) Continuation of application No. 16/254,097, filed on Jan. 22, 2019, now Pat. No. 11,484,469.

(51) Int. Cl.
*A61J 1/20* (2006.01)
*A61M 39/20* (2006.01)
*A61J 1/10* (2006.01)

(52) U.S. Cl.
CPC ............. *A61J 1/201* (2015.05); *A61J 1/2013* (2015.05); *A61J 1/2075* (2015.05); *A61J 1/2089* (2013.01); *A61M 39/20* (2013.01); *A61J 1/10* (2013.01)

(58) Field of Classification Search
CPC ........ A61J 1/201; A61J 1/2089; A61J 1/2013; A61J 1/2075; A61J 1/2096; A61M 5/1409; A61M 39/20
See application file for complete search history.

(56) References Cited

U.S. PATENT DOCUMENTS

| 4,534,758 A | 8/1985 | Akers et al. |
| 4,573,967 A | 3/1986 | Hargrove et al. |

(Continued)

FOREIGN PATENT DOCUMENTS

| EP | 0416454 | 3/1991 |
| EP | 1454650 | 9/2004 |

(Continued)

OTHER PUBLICATIONS

International Search Report and Written Opinion for International App. No. PCT/US2020/014412 dated Jan. 18, 2021 (7 pages).

(Continued)

*Primary Examiner* — Erich G Herbermann
*Assistant Examiner* — Seth Han
(74) *Attorney, Agent, or Firm* — K&L Gates LLP

(57) ABSTRACT

A reconstitution device includes a body, a first piercing member located at a first end of the body, and a receptacle located at the second end of the body. The receptacle includes a collar configured to engage a vial, and a cap extending from the collar and holding a second piercing member. The second piercing member is disposed within the collar. The reconstitution device includes a first fluid pathway formed within and extending from the first piercing member to the second piercing member. The reconstitution device includes a second fluid pathway formed within and extending from the second piercing member to a portion of the body between the first piercing member and the second piercing member.

20 Claims, 7 Drawing Sheets

(56) References Cited

U.S. PATENT DOCUMENTS

| | | | |
|---|---|---|---|
| 4,834,152 A | 5/1989 | Howson et al. | |
| 4,936,829 A | 6/1990 | Zdeb et al. | |
| 5,116,316 A | 5/1992 | Sertic et al. | |
| 5,636,660 A | 6/1997 | Pfleiderer et al. | |
| 5,853,406 A | 12/1998 | Masuda et al. | |
| 5,897,526 A * | 4/1999 | Vaillancourt | A61M 5/1407 604/82 |
| 6,386,367 B1 | 5/2002 | Bayliss | |
| 6,948,522 B2 * | 9/2005 | Newbrough | A61J 1/2089 137/550 |
| 7,074,216 B2 | 7/2006 | Fowles et al. | |
| 7,294,122 B2 | 11/2007 | Kubo et al. | |
| 8,167,863 B2 | 5/2012 | Yow | |
| 8,821,436 B2 | 9/2014 | Mosler et al. | |
| 9,345,640 B2 | 5/2016 | Mosler et al. | |
| 2011/0087164 A1 * | 4/2011 | Mosler | A61J 1/2089 604/87 |
| 2012/0053555 A1 * | 3/2012 | Ariagno | A61J 1/2089 604/416 |

FOREIGN PATENT DOCUMENTS

| | | |
|---|---|---|
| WO | 86/01712 | 3/1986 |
| WO | 2017/118503 | 7/2017 |

OTHER PUBLICATIONS

International Preliminary Report on Patentability for International App. No. PCT/US2020/014412 dated Apr. 26, 2021 (23 pages).
International Search Report and Written Opinion for International App. No. PCT/US2020/014412 dated May 6, 2020 (172 pages).
European Office Action dated Feb. 6, 2023 for App. No. 20 708 272.8-1113 (5 pages).
European Office Action dated Aug. 10, 2023 for App. No. 20 708 272.8-1113 (5 pages).

\* cited by examiner

RECONSTITUTION SYSTEM TO ADMINISTER A DRUG VIA A HIGH VACUUM VIAL WITH INTEGRATED VENT CONDUIT

CROSS-REFERENCE TO RELATED APPLICATIONS

The present application is a continuation of U.S. patent application Ser. No. 16/254,097, filed on Jan. 22, 2019, the disclosure of which is incorporated herein by reference for all purposes.

BACKGROUND

Medical therapy often requires the intravenous administration of fluids to correct electrolyte imbalance, medicated solutions, and/or nutrients to provide nutrition to patients unable to receive oral or enteral nutrition. Intravenous ("IV") fluids are generally available in aseptic single- or multi-chamber flexible containers that include an administration port and a medication port. An IV administration set is typically inserted into a flexible container, such as a multi-chamber IV bag, via the administration port to allow administration of the fluids from the flexible container to the patient. Likewise, medications and/or nutrients can be injected, into the flexible container, via the medication port.

Certain active agents, such as medications and nutrients, which may be unstable in liquid form, are stored in dry form. For example, active agents may be unstable at the pH of the IV fluid, susceptible to damage via light, or have other instability, thus requiring dry form storage. Dry form active agents may be stored in glass vials, sealed with rubber stoppers, or be stored in other containers such as plastic containers, ampoules, or in small bags that may be closed with standard screw caps. Prior to being administered to a patient, the dry form active agents are reconstituted. Reconstitution typically includes the removal of a protective cover to expose the rubber stopper, wiping the stopper with an antiseptic wipe, adding a diluent to the vial by inserting a needle of a syringe through the rubber stopper and depositing the contents of the syringe, such as the diluent, into the vial, and shaking the vial to fully dissolve or suspend the active agents. Subsequently, the resulting reconstituted solution or suspension is withdrawn from the vial by inserting a needle of a syringe through the rubber stopper, aspirating the solution or suspension into the syringe, and injecting the contents of the syringe into the flexible container via the medication port.

The above procedure is cumbersome and prone to spillage. An improved system and method for using a reconstitution device to administer medications via IV bags, is needed accordingly.

SUMMARY

To improve the administration of medications via IV bags, a patient medication delivery paradigm is provided herein. To implement an improved way of medication administration, a reconstitution device, system, and method is disclosed. More specifically, a reconstitution device is provided to establish a fluid pathway between a source (e.g., a drug vial) and a location (e.g., an intravenous ("IV") bag), which includes a vent conduit to improve reconstitution, especially with respect to multi-chamber bags.

In light of the disclosure herein, and without limiting the scope of the invention in any way, in a first aspect of the present disclosure, which may be combined with any other aspect listed herein unless specified otherwise, a reconstitution device includes a body, a first piercing member located at a first end of the body, and a receptacle located at the second end of the body. The receptacle includes a collar configured to engage a vial, and a cap extending from the collar and holding a second piercing member. The second piercing member is disposed within the collar. The reconstitution device includes a first fluid pathway formed within and extending from the first piercing member to the second piercing member. The reconstitution device includes a second fluid pathway formed within and extending from the second piercing member to a portion of the body between the first piercing member and the second piercing member.

In a second aspect of the present disclosure, which may be combined with any other aspect listed herein unless specified otherwise, the cap is formed integrally with the collar.

In a third aspect of the present disclosure, which may be combined with any other aspect listed herein unless specified otherwise, the collar is cylindrical and is configured to concentrically engage the vial.

In a fourth aspect of the present disclosure, which may be combined with any other aspect listed herein unless specified otherwise, the collar engages the vial, such that the second piercing member extends into the vial, and such that the second piercing member is placed in fluid communication with the vial.

In a fifth aspect of the present disclosure, which may be combined with any other aspect listed herein unless specified otherwise, the first piercing member is configured to pierce an intravenous ("IV") bag port, such that the first piercing member is placed in fluid communication with the IV bag port.

In a sixth aspect of the present disclosure, which may be combined with any other aspect listed herein unless specified otherwise, the second fluid pathway forms a vent conduit.

In a seventh aspect of the present disclosure, which may be combined with any other aspect listed herein unless specified otherwise, a removable plug is fitted within the second fluid pathway at the portion of the body between the first piercing member and the second piercing member.

In a eighth aspect of the present disclosure, which may be combined with any other aspect listed herein unless specified otherwise, the removable plug forms a hermetic seal with the portion of the body between the first piercing member and the second piercing member.

In a ninth aspect of the present disclosure, which may be combined with any other aspect listed herein unless specified otherwise, the vial is initially sealed under a vacuum.

In a tenth aspect of the present disclosure, which may be combined with any other aspect listed herein unless specified otherwise, a reconstitution system includes a drug vial, a fluid container, and a reconstitution device. The reconstitution device includes a body, a first piercing member located at a first end of the body, and a receptacle located at a second end of the body. The receptacle includes a collar configured to engage the drug vial, and a cap extending from the collar and holding a second piercing member. The second piercing member is disposed within the collar. The reconstitution device includes a first fluid pathway formed within and extending from the first piercing member to the second piercing member. The reconstitution device includes a second fluid pathway formed within and extending from the second piercing member to a portion of the body between the first piercing member and the second piercing member.

In a eleventh aspect of the present disclosure, which may be combined with any other aspect listed herein unless specified otherwise, the first piercing member extends into the fluid container, and the collar engages the drug vial such that the second piercing member extends into the drug vial, and such that the fluid container is placed in fluid communication with the drug vial via the first fluid pathway.

In a twelfth aspect of the present disclosure, which may be combined with any other aspect listed herein unless specified otherwise, the reconstitution system further includes a plug disposed along the portion of the body between the first piercing member and the second piercing member.

In a thirteenth aspect of the present disclosure, which may be combined with any other aspect listed herein unless specified otherwise, the plug is removable and, responsive to the plug being removed, the drug vial is placed in fluid communication with an external environment via the second fluid pathway.

In a fourteenth aspect of the present disclosure, which may be combined with any other aspect listed herein unless specified otherwise, air from the external environment (i) flows into the drug vial via the second fluid pathway, and (ii) pushes a reconstituted solution from the drug vial into the fluid container via the first fluid pathway.

In a fifteenth aspect of the present disclosure, which may be combined with any other aspect listed herein unless specified otherwise, the drug vial contains one of a pharmaceutical agent or a nutritional supplement.

In a sixteenth aspect of the present disclosure, which may be combined with any other aspect listed herein unless specified otherwise, the drug vial is initially sealed under a vacuum.

In a seventeenth aspect of the present disclosure, which may be combined with any other aspect listed herein unless specified otherwise, the drug vial is formed of an ultraviolet ("UV") light blocking material.

In a eighteenth aspect of the present disclosure, which may be combined with any other aspect listed herein unless specified otherwise, the reconstitution system further includes an intravenous ("IV") line positioned and arranged to deliver a fluid from the fluid container to a patient.

In a nineteenth aspect of the present disclosure, which may be combined with any other aspect listed herein unless specified otherwise, the reconstitution system further includes an infusion pump in operable communication with the IV line.

In a twentieth aspect of the present disclosure, which may be combined with any other aspect listed herein unless specified otherwise, a drug reconstitution method includes enabling engagement of a first piercing member with a fluid container and enabling engagement of a second piercing member with a drug vial, such that intravenous ("IV") fluid may flow along a first fluid pathway formed within and extending from the fluid container to the drug vial. The method includes enabling mixing of the IV fluid with an agent located within the drug vial to form a mixed drug. The method includes enabling removal of a plug, such that air from an external environment may flow along a second fluid pathway formed within and extending from the external environment to the drug vial. Air pressure in the external environment causes air to (i) flow into the drug vial via the second fluid pathway, and (ii) push the mixed drug from the drug vial to the fluid container via the first fluid pathway.

In a twenty first aspect of the present disclosure, any of the structure, functionality, and alternatives discussed in connection with any of FIGS. 1 to 7 may be combined with any of the structure, functionality, and alternatives discussed in connection with any other one or more of FIGS. 1 to 7.

In light of the disclosure and aspects set forth herein, it is accordingly an advantage of the present disclosure to provide a reconstitution system that ensures complete reconstitution and subsequent infusion of a drug from a drug vial directly into a flexible container.

It is another advantage of the present disclosure to provide a reconstitution system that reduces drug degradation by reconstituting the drug and immediately delivering it to the flexible container. The particular system may be further configured to limit environmental degradation by avoiding solution-interaction with outside factors, such as light or air.

It is a further advantage of the present disclosure to provide a reconstitution system that ensures the contents of the vial, such as the reconstituted drug, are diluted prior to being administrated to the patient to prevent any medical or efficacy risks based on osmolarity.

It is yet another advantage of the present disclosure to provide a ready-to-use reconstitution system configured to accept vials directly.

It is yet a further advantage of the present disclosure to provide a reconstitution system avoiding tedious preparation steps involved with typical dried drug reconstitution by accepting vials directly.

It is still another advantage of the present disclosure to pre-plug the vial to ensure that drug prescriptions and deliveries are not inadvertently missed by medical professionals.

In yet another advantage of the present disclosure, each discrete component of the reconstitution system may be processed, sterilized, and handled separately on a component-by-component basis.

In yet a further advantage of the present disclosure, the reconstitution device may be particularly applicable for use with multi-chamber IV bags.

Moreover, an advantage of the present disclosure is to provide a reconstitution system ensuring that microbiological contamination risk is minimized by accepting pre-plugged vials in a sterile manner.

Additional features and advantages of the disclosed devices, systems, and methods are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein. Moreover, it should be noted that the language used in the specification has been selected for readability and instructional purposes, and not to limit the scope of the inventive subject matter.

BRIEF DESCRIPTION OF THE FIGURES

Understanding that figures depict only typical embodiments of the invention and are not to be considered to be limiting the scope of the present disclosure, the present disclosure is described and explained with additional specificity and detail through the use of the accompanying figures. The figures are listed below.

DETAILED DESCRIPTION

Figure 1:
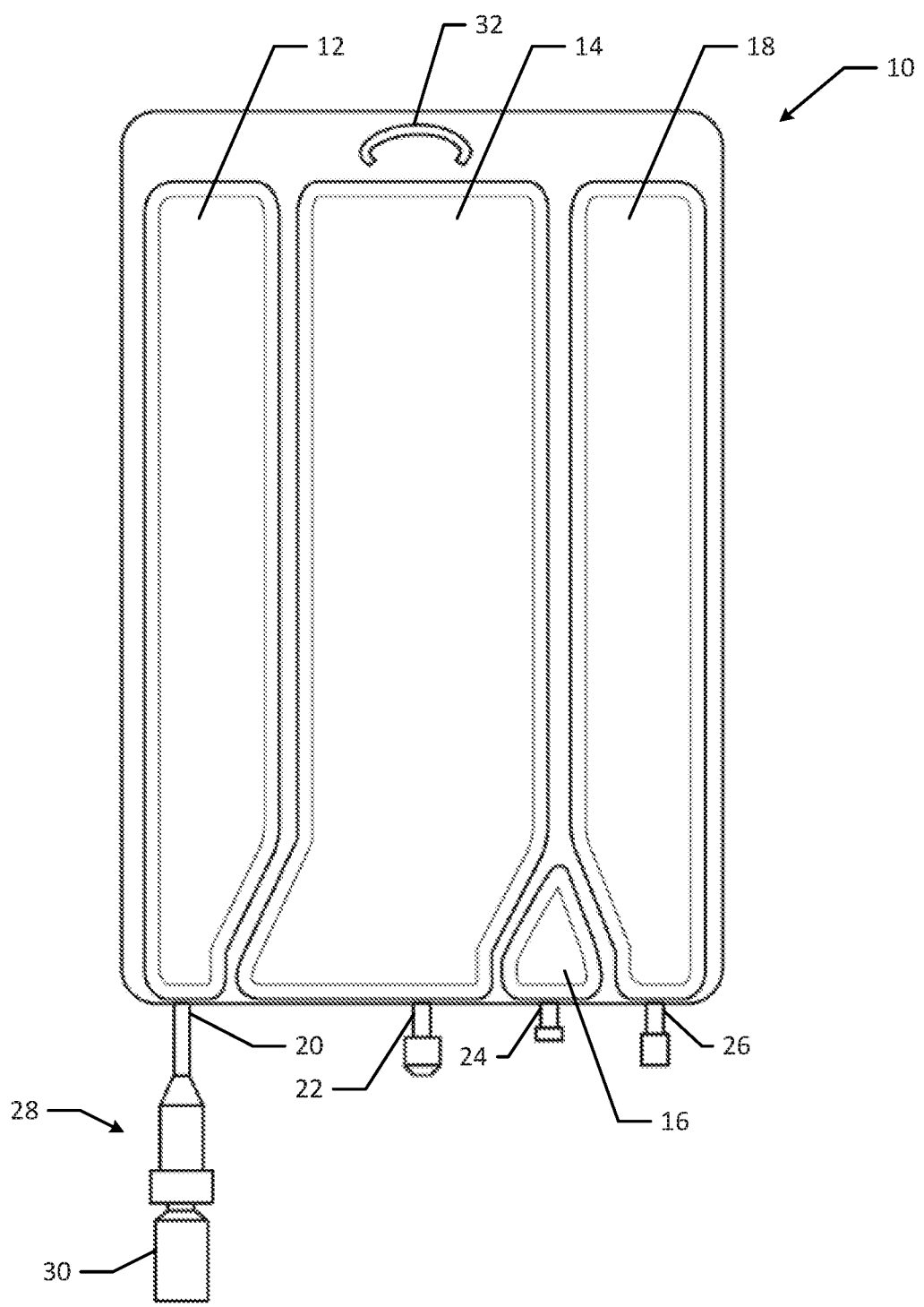
FIG. 1 is a top plan view of a reconstitution device, drug vial, and multi-chamber bag, according to an example embodiment of the present disclosure.

Certain embodiments described herein relate generally to the field of intravenous ("IV") administration of an active agent. More particularly, some embodiments described herein relate to the reconstitution of an active agent in a vial, delivery to a flexible container, and subsequent IV administration of the active agent using the flexible container and an IV administration set.

As discussed herein, adding a dried drug to an IV bag typically includes several tedious steps. For example, a medical professional may be required to remove a protective cover from a vial, wipe a stopper of the vial, add diluent to the vial, and shake the vial. The drug then has to be withdrawn from the vial and injected into, for example, an IV bag.

Typical commercially available vial reconstitution systems (e.g., the Baxter Vial-Mate™ system) are configured such that the drug contained in the vial is added into a single chamber IV bag directly, via a port. In such systems, the drug from the vial is mixed with fluid within the entire single chamber IV bag, such as saline, prior to being administered to the patient. For example, the drug is delivered into the single chamber IV bag, via a medication port, mixes with the fluid of the single chamber IV bag, and is then administered to the patient via an administration port (e.g., by an IV set connected to the single chamber IV bag at the administration port). In this delivery paradigm, once the vial is connected to the IV bag, pressure is applied onto the IV bag to "push" liquid from the IV bag into the vial, for reconstituting the drug. The system is then flipped upside down, and pressure is applied to the bag to "push" headspace gas from the IV bag into the vial. The headspace gas consequently forces the reconstituted drug back into the IV bag.

The above delivery paradigm is particularly problematic with multi-chamber IV bags, which typically have frangible seals that open when pressure is applied to the bag. Further, multi-chamber IV bags are typically underfilled, thus making it difficult if not impossible to apply pressure to "push" headspace gas into the vial.

The reconstitution devices, systems, and methods disclosed herein are configured so that the vial containing the drug is connected directly with the multi-chamber IV bag. The connection allows for both an initial reconstitution in the vial, permitting fluid to flow from the multi-chamber IV bag to the vial, and a secondary reconstitution as the reconstituted drug travels directly into the multi-chamber IV bag from the vial. Implementation of an integrated vent conduit ensures that reconstituted solution can travel back into the IV bag, without requiring the application of pressure at the IV bag for "pushing" headspace gases. Thus, the devices, systems, and methods disclosed herein are particularly applicable in circumstances concerning underfilled bags, such as multi-chamber IV bags. The present configuration enhances the efficacy by which a drug is reconstituted in the vial and delivered subsequently to a patient. Further, the vial may initially be sealed and placed under a vacuum, thus eliminating the need to "push" liquid from the IV bag into the vial. When initially reconstituted, the vacuum may further enhance the efficacy by which a drug is reconstituted in a vial.

Referring now to the drawings and in particular to FIG. 1, one embodiment of the reconstitution device and multi-chamber bag of the present disclosure is illustrated. Multi-chamber bag 10 includes several discrete chambers separated by frangible barriers, including first chamber 12, second chamber 14, third chamber 16, and fourth chamber 18. It should be appreciated that multi-chamber bag 10 could include more, or less, than four chambers. In an embodiment, first chamber 12 holds lipids in liquid form, second chamber 14 holds amino acids in liquid form, third chamber 16 holds trace elements in liquid form, and fourth chamber 18 holds glucose in liquid form. Each of the chambers 12, 14, 16, 18 includes a respective administration port 20, 22, 24, 26. Multi-chamber bag 10 may be constructed of any suitable plastic or rubber material, such as polyvinyl chloride ("PVC"), non-DEHP PVC, Krayton polypropylene mixture, or other similar materials.

As illustrated, reconstitution device 28 engages with administration port 20 (associated with first chamber 12). It should be appreciated that reconstitution device 28 could engage with any of the administration ports and/or chambers mentioned above. Reconstitution device 28 also engages with a vial 30, discussed in greater detail herein. Any of the device engagements discussed herein may be via a luer connector, tube connector, snap fit, interference fit, or any other related means for connection. Via the vial engagement, a dried drug from vial 30 is reconstituted with fluid from the first chamber 12, or alternatively several chambers if their seals have been broken, and the reconstituted drug is subsequently delivered into multi-chamber bag 10, for further reconstitution with the entire multi-chamber bag 10 and future delivery to a patient. For example, multi-chamber bag 10 may further include a port or connection for engagement with an IV delivery tube, connected to a patient. Multi-chamber bag 10 may further include a loop 32, for hanging the bag on a stand, as discussed in greater detail herein.

Figure 2:
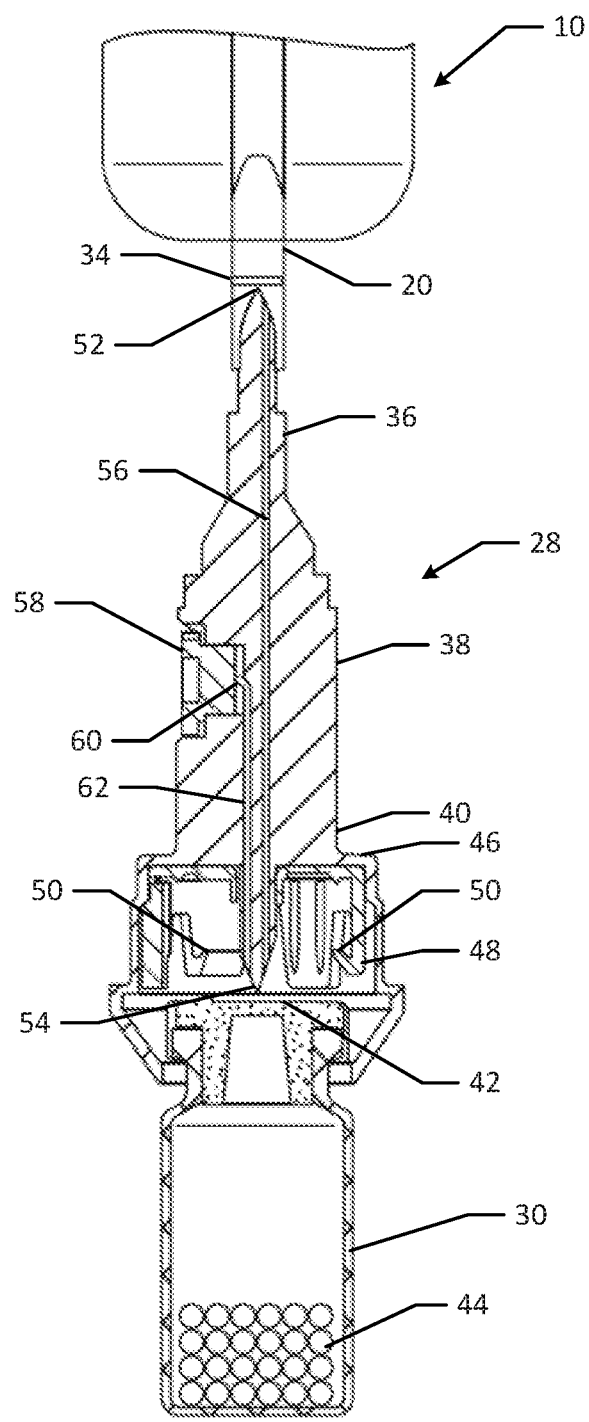
FIG. 2 is a sectioned elevation view of a reconstitution device, drug vial, and multi-chamber bag, according to an example embodiment of the present disclosure.

FIG. 2 is a sectioned view of the reconstitution device 28 and multi-chamber bag 10 of FIG. 1, according to an example embodiment of the present disclosure. As illustrated, multi-chamber bag 10 initially includes a membrane 34 at administration port 20.

Reconstitution device 28 includes a piercing end 36, a body 38, and a retaining end 40. Reconstitution device 28 may be constructed of any suitable plastic or rubber material, such as polyvinyl chloride ("PVC"), non-DEHP PVC, Krayton polypropylene mixture, or other similar materials.

Retaining end 40 is configured to engage vial 30 (e.g., via concentric engagement). Vial 30 may be fitted with a stopper 42, which may be a rubber stopper, a plastic stopper, and/or include a foil cover, or be any other similar structure for sealing vial 30. Stopper 42 may protect the contents of vial 30 from environmental factors, such as ambient air. In an embodiment, the contents of vial 30 include a dried drug 44.

In an embodiment, vial 30 is formed of an ultraviolet ("UV") light blocking material, which may further protect the contents of vial 30 from environmental factors, such as light.

Specifically, regarding the concentric engagement of device 28 to vial 30, retaining end 40 of reconstitution device 28 includes a cap 46. Retaining end 40 further includes a cylindrical collar 48. Cap 46 may be formed integrally with collar 48, or be attached to retaining end 40. In alternative embodiments, collar 48 may have differently shaped cross-sections (e.g., hexagonal, square, triangular, or other suitable geometric shape). Cylindrical collar 48 is configured to engage vial 30 (e.g., via concentric engagement).

In the illustrated embodiment, the stopper-side of vial 30 may be received within cylindrical collar 48 of device 28, such that the cylindrical collar 48 is disposed around the outside of the stopper-side of vial 30. Vial 30 typically contains an active agent such as a pharmaceutical agent or a nutritional supplement. The active agent may be present as a dried drug 44, such as a powder obtained by lyophilization. Alternatively, the active agent is present in an aqueous solution or suspension, or other typical liquid form. The inner surface of collar 48 may include a plurality of ridges 50 that are configured to engage, e.g., via a spring-like deformation, to press-fit or snap-fit over the stopper-side of vial 30, such that the stopper-side of vial 30 is retained inside the plurality of ridges 50 of the collar 48.

Reconstitution device 28 further includes a first piercing member 52 and a second piercing member 54. First piercing member 52 and second piercing member 54 may be made of metal (e.g., stainless steel), medical grade plastic, or other suitable material. A first fluid pathway 56 extends between first piercing member 52 and second piercing member 54. Specifically, cap 46 extends from collar 48 and holds second piercing member 54. Second piercing member 54 is disposed within collar 48. As configured, first piercing member 52 is configured to engage with administration port 20 of multi-chamber bag 10; likewise, second piercing member 54 is configured to engage with vial 30. In an embodiment, at least one of the first piercing member 52 or the second piercing member 54 may include or form a syringe needle or a plastic spike.

Reconstitution device 28 further includes a plug 58, disposed along a portion of body 38 between piercing end 36 and retaining end 40. Specifically, plug 58 may be removably attached to a receptacle 60 along body 38. Generally, plug 58 is configured to form a hermetic seal with receptacle 60 when engaged. In various embodiments, plug 58 engages with receptacle 60 via a threaded fit, snap fit, or other suitable fit. In an embodiment, plug 58 further includes an o-ring or other gasket. A second fluid pathway 62 extends between receptacle 60 and second piercing member 54.

Figure 3:
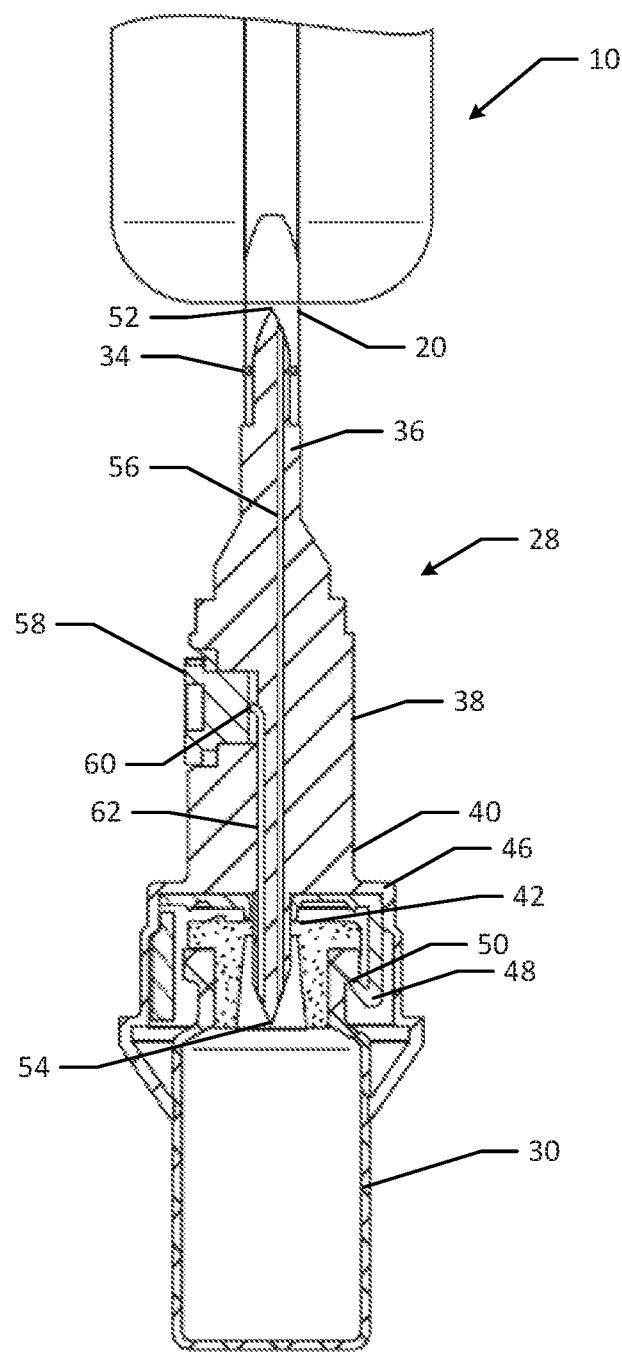
FIG. 3 is a sectioned elevation view of a reconstitution device and drug vial engaging with a multi-chamber bag, according to an example embodiment of the present disclosure.

FIG. 3 is a section view of the reconstitution device 28 of FIG. 1, further illustrating the engagement with multi-chamber bag 10, according to an example embodiment of the present disclosure. As previously illustrated with respect to FIG. 2, FIG. 3 also shows administration port 20 of multi-chamber bag 10 includes membrane 34 (e.g., a removable membrane or a pierceable membrane). Membrane 34 may initially prevent premature flow from multi-chamber bag 10. Membrane 34 may further ensure that a vacuum exists within the various fluid pathways communicating with vial 30 during reconstitution, to advantageously generate pressurized fluid streams for reconstitution, as described in greater detail below. Membrane 34 may also reduce or eliminate leakage from multi-chamber bag 10.

First piercing member 52 is, in the illustrated embodiment, configured to pierce an administration port (e.g., an IV bag port) at membrane 34, so that the first piercing member 52 is in fluid communication with administration port 20 and thus with multi-chamber bag 10. Administration port 20 may be connected to multi-chamber bag 10 or may be formed integrally with multi-chamber bag 10.

As illustrated in FIG. 3, vial 30 is engaged within collar 48 such that second piercing member 54 pierces stopper 42 of vial 30. In one embodiment, the user pushes vial 30 onto cap 46 to secure engagement between the vial 30 and the collar 48. In one embodiment, second piercing member 54 pierces through the stopper 42 (e.g., a rubber stopper) of vial 30 and extends into vial 30. In a related embodiment, engagement between the collar 48 and the vial 30 may further include rotation or twisting of the vial 30. For example, the collar 48 may include inner threads, and the vial 30 may include outer threads, such that a threaded engagement between the vial 30 and the collar 48 is implemented for secure engagement between the components.

Once engaged, multi-chamber bag 10 is in fluid communication with the vial 30 via first fluid pathway 56 that extends from first piercing member 52 to second piercing member 54. In an embodiment, vial 30 is initially sealed and under a vacuum, prior to engagement with collar 48 (e.g., a low pressure such as 100 mbar, which is less than ambient air pressure).

It should be appreciated that the piercing described above for first piercing member 52 and second piercing member 54 happens nearly simultaneously in one embodiment. For example, once first piercing member 52 pierces the administration port 20 (e.g., an IV bag port) at membrane 34, first piercing member 52 is in fluid communication with administration port 20; thus, liquid may flow from administration port 20 into the reconstitution device 28 via the first fluid pathway 56. To ensure that liquid does not inadvertently spill out of the second piercing member 54 (e.g., via first fluid pathway 56), the second piercing member 54 pierces stopper 42 of vial 30 immediately after the first piercing member 52 pierces the administration port 20 (e.g., nearly simultaneously). In this way, inadvertent spilling is prevented.

After the piercing of members 52 and 54, fluid in multi-chamber bag 10 may flow directly from the first piercing member 52 to the second piercing member 54 via the first fluid pathway 56, and consequently into vial 30. Flow into vial 30 via first fluid pathway 56 can be characterized as a pressurized fluid stream (e.g., jet stream). Because vial 30 was initially sealed and under a vacuum prior to engagement with collar 48, engagement causes fluid from multi-chamber bag 10 to be rapidly drawn into vial 30 by the negative pressure. The initial draw of fluid may generate a pressurized fluid stream from the second piercing member 54 (e.g., a jet stream) into vial 30. In certain embodiments, a pressurized fluid stream is advantageous for mixing and reconstituting a dried drug within vial 30. The magnitude of the vacuum in vial 30 may be adjusted, to obtain an optimal mixing effect and/or to obtain the desired filling volume. The vacuum also aids in reducing or eliminating problems in removing air compared to vial 30 instead being under atmospheric pressure. As fluid from multi-chamber bag 10 flows into vial 30, dried drug 44 is reconstituted. Dried drug 44 illustrated in FIG. 2 is no longer shown in FIG. 3 because the drug has been reconstituted with fluid from multi-chamber bag 10.

The reconstituted drug within vial 30 next needs to be sent back into multi-chamber bag 10. Reconstitution device 28 is capable of performing this operation via second fluid pathway 62, also referred to herein as a vent or vented conduit. The process of flowing the reconstituted drug back into bag 10 is performed in connection with FIGS. 4 to 6, which illustrate engagement of reconstitution device 28 to multi-chamber bag 10, according to example embodiments of the present disclosure.

Figure 4:
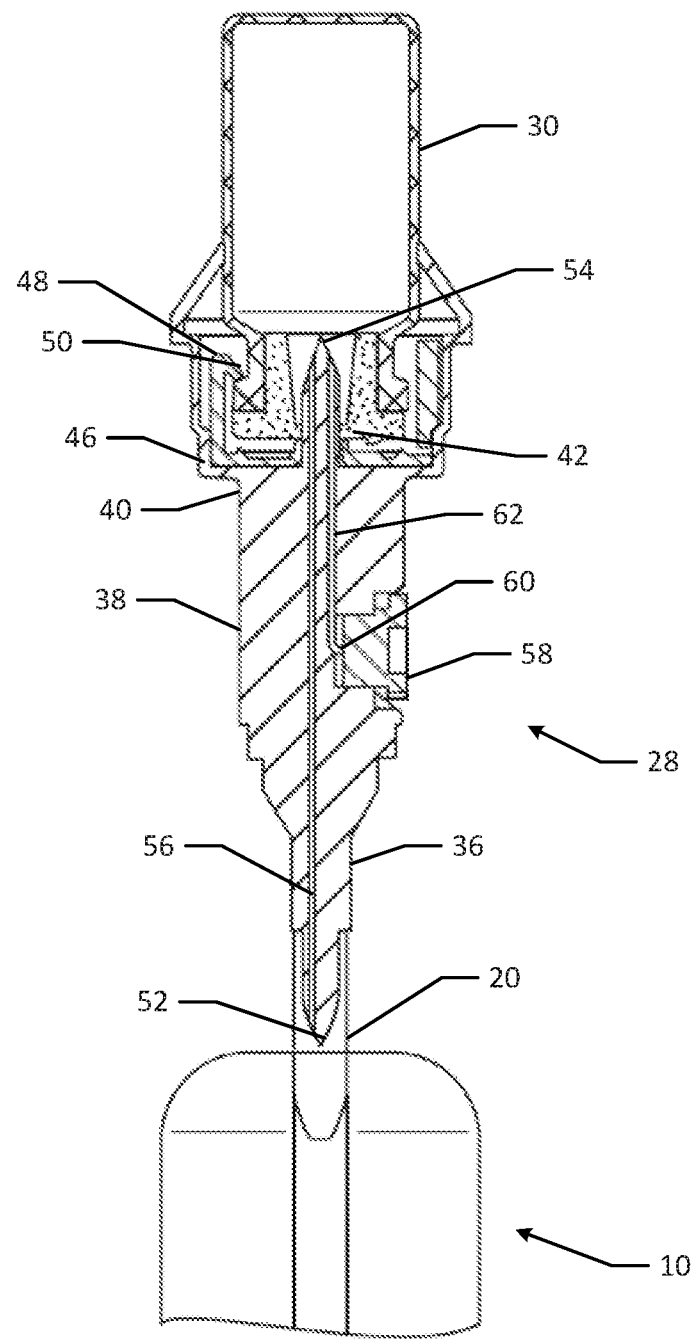
FIG. 4 is a rotated sectioned elevation view of the reconstitution device and drug vial engaging with a multi-chamber bag of FIG. 1, according to an example embodiment of the present disclosure.
Figure 5:
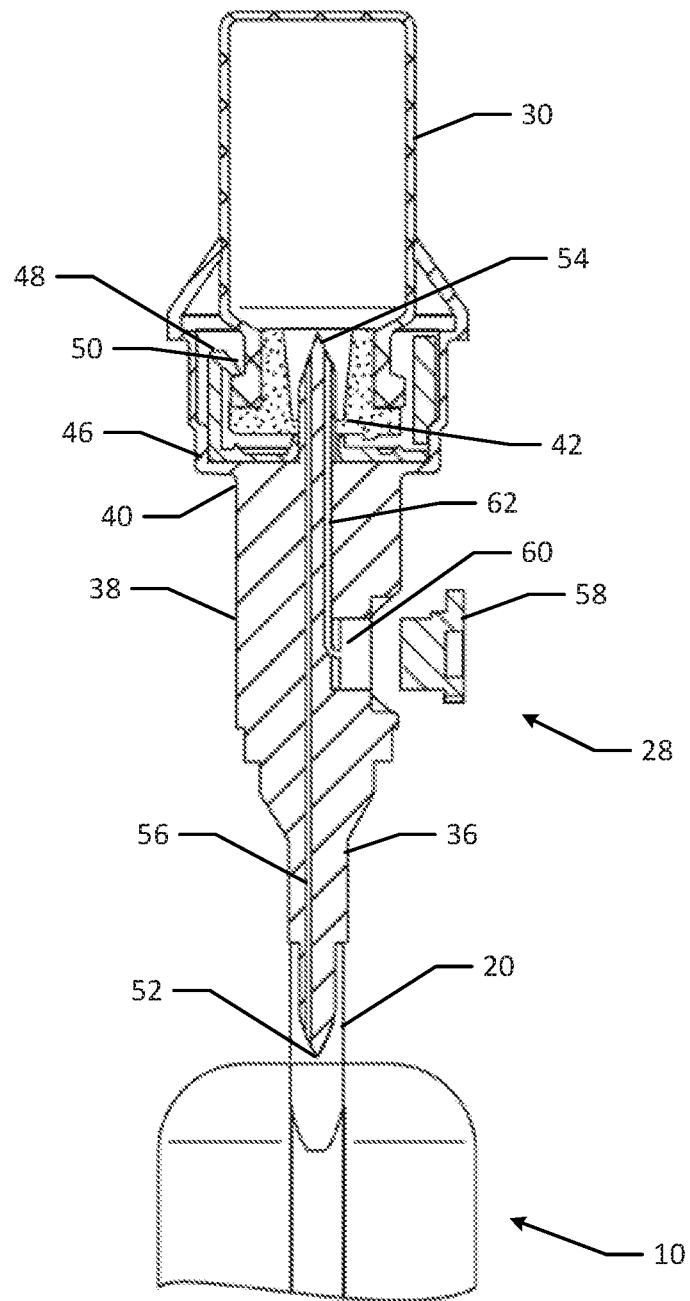
FIG. 5 is a sectioned elevation view of a reconstitution device and drug vial engaging with a multi-chamber bag during plug removal, according to an example embodiment of the present disclosure.

As illustrated in FIG. 4, reconstitution device 28 and related vial 30 are rotated vertically to an upside-down configuration. Plug 58 is then removed from receptacle 60, as illustrated by FIG. 5. Alternatively, instead of physically removing plug 58, the user merely moves plug 58 from a closed state to an opened state. By removing plug 58 from receptacle 60 (or opening plug 58), vial 30 is placed in fluid communication with an external environment, such as a medical preparation room, via second fluid pathway 62. In an embodiment, reconstitution device 28 further includes an air filter, such as a 0.22 µm air filter, disposed along receptacle 60 between plug 58 and second fluid pathway 62. In a different embodiment, the air filter is disposed along second fluid pathway 62.

Figure 6:
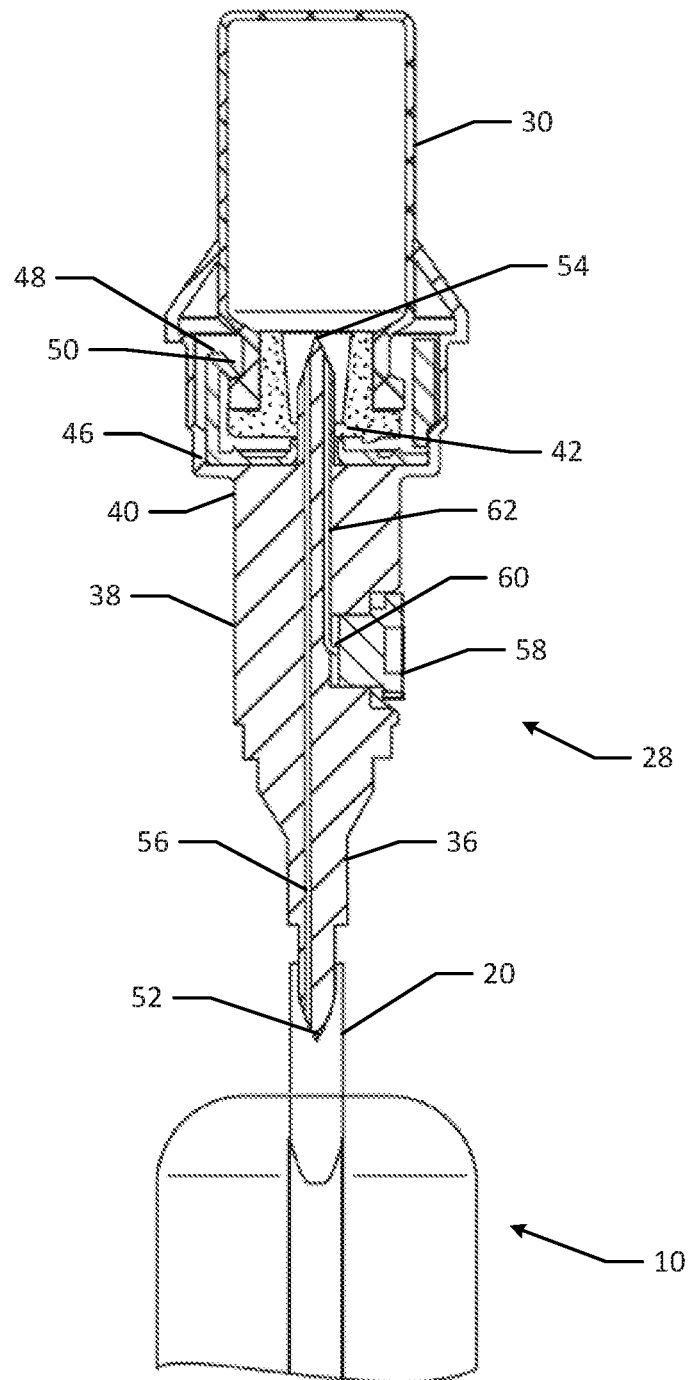
FIG. 6 is a sectioned elevation view of a reconstitution device and drug vial engaging with a multi-chamber bag during plug reattachment, according to an example embodiment of the present disclosure.

As previously noted, vial 30 is initially sealed and under a vacuum. Likewise, the contents of multi-chamber bag 10 are sealed at a lower pressure. Thus, the entire system, prior to removal of plug 58, is at a sub-atmospheric pressure. For this reason, removal of plug 58 causes atmospheric air from the external environment to flow into vial 30 via second fluid pathway 62, and subsequently push the reconstituted material from the vial 30 to multi-chamber bag 10 via first fluid pathway 56. Once reconstituted material flows into multi-chamber bag 10, plug 58 is then re-attached to receptacle 60 (or closed), as illustrated by FIG. 6.

In an alternate embodiment, reconstitution device 28 may additionally or alternatively include a valve to replace plug 58. For example, a user-operated valve may be implemented, such that the user may selectively open and close receptacle 60 via the valve, thereby controlling when second fluid pathway 62 communicates with the external environment. In a related embodiment, user-operated valve may further provide the user with the ability to selectively open and close first fluid pathway 56. It should be appreciated that the user-operated valve may be positioned at any location along reconstitution device 28 and/or there could be multiple valves (e.g., one valve for each of first fluid pathway 56 and second fluid pathway 62). In various embodiments, the user-operated valve may be a ball valve, a gate valve, a globe valve, a check valve, or other related valves.

In an alternate embodiment, reconstitution device 28 may be implemented with an IV bag that is initially empty and under a vacuum or partial vacuum. For example, the reconstitution device 28 with vial 30 is connected to an empty IV bag (e.g., via administration port 20). The empty IV bag may then be subsequently filled with any desired solution, such as saline or glucose, through a dedicated port. This may be advantageous for applications where providing the solution ahead of time is costly or difficult. In this alternative embodiment, the solution for the IV bag may be prepared and the IV bag may be filled during administration. As solution is added to the empty IV bag (that is already connected to reconstitution device 28), reconstitution may occur as described above.

Figure 7:
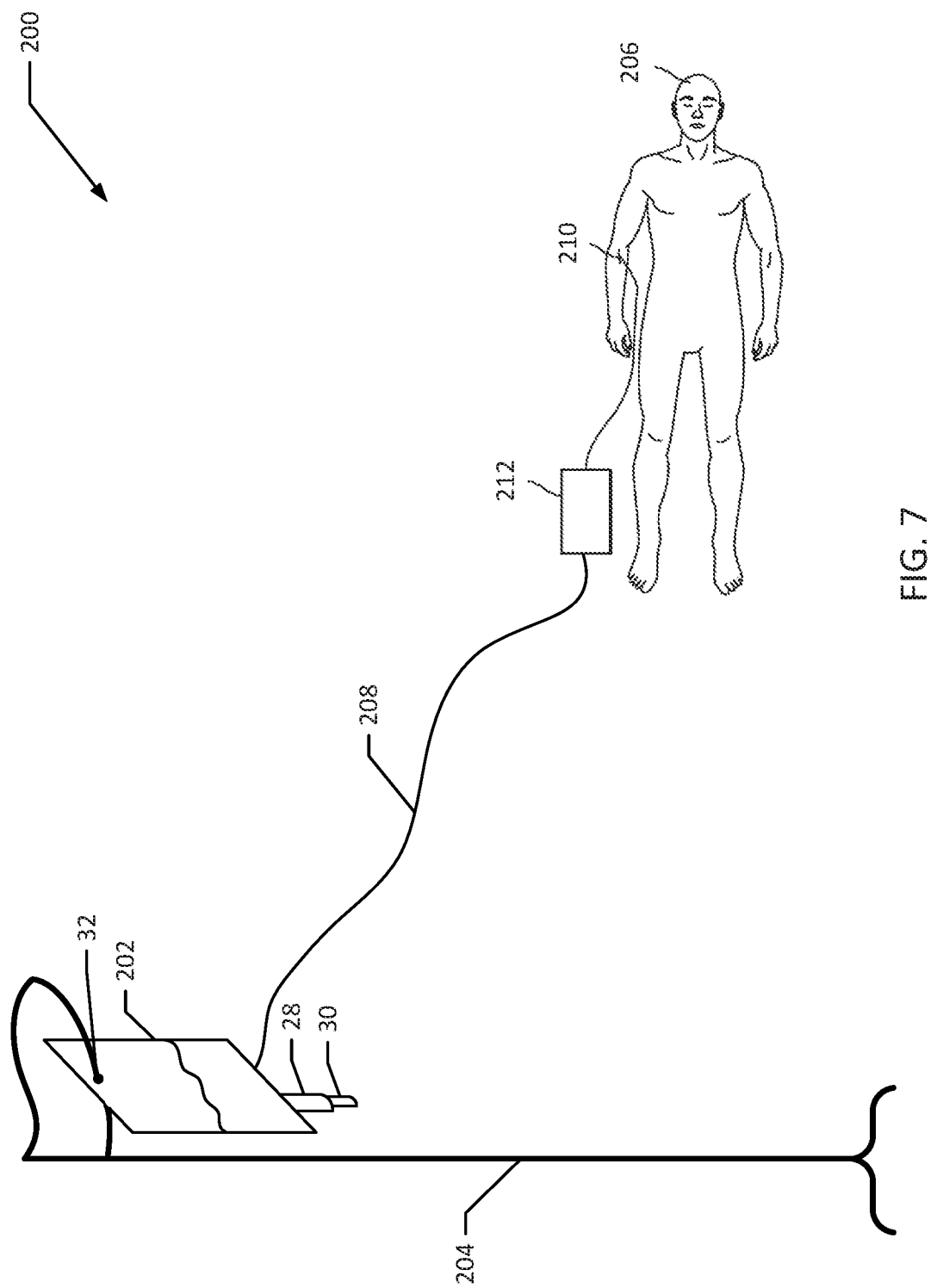
FIG. 7 is a schematic view of one embodiment of a system employing any of the reconstitution devices described herein.

FIG. 7 illustrates one embodiment of a system 200 employing reconstitution device 28, which is configured to engage with drug vial 30 as described above. System 200 includes an IV bag 202 (e.g., multi-chamber bag 10) hanging from a stand 204 (e.g., via loop 32). The IV bag 202 may include a fluid, such as saline, glucose, or other similar fluid, for delivery to a patient 206. As illustrated, IV bag 202 is positioned on the stand 204 to ensure that the IV bag 202 is located vertically above the patient 206, which ensures that fluid in the IV bag 202 gravity flows to patient 206. Furthermore, the IV bag 202 is illustrated as a single-chamber in FIG. 7; it should be appreciated, however, that IV bag 202 is alternatively a multi-chamber bag (e.g., multi-chamber bag 10 illustrated in FIG. 1), and that the seals between chambers have already been opened in FIG. 7.

System 200 as illustrated includes reconstitution device 28 and vial 30. Reconstitution device 28 is connected to IV bag 202 as previously described using first piercing member 52, while vial 30 is connected as previously described using second piercing member 54. A delivery tube 208, such as an IV tube, engages with IV bag 202. Delivery tube 208 is also connected to patient 206 at an IV location 210. For example, delivery tube 208 may extend to an intra-venous needle inserted into the patient 206 at the IV location 210.

Delivery tube 208 is configured to convey the fluid in the IV bag 202, mixed with drug 44 from vial 30 in IV bag 202, to the patient 206 at IV location 210. While fluid conveyance may be facilitated via gravity due to IV bag 202 being elevated on the stand 204, additional or alternative modes of fluid conveyance may be implemented. For example, system 200 may use an infusion pump 212, which may for example be a Sigma™ Large Volume Pump ("LVP") provided by the assignee of the present disclosure. Infusion pump 212 may control fluid conveyance along delivery tube 208 (e.g., from the IV bag 202 to the patient 206 at the IV location 210). In such a case, bag 202 may be located even or vertically below patient 206.

With reference to FIGS. 3 and 7, the fluid in the IV bag 202 may travel into the first piercing member 52 and subsequently travel into the vial 30, via the first fluid pathway 56. The fluid mixes with drug 44 in vial 30 to form a reconstituted solution. Upon flipping of reconstitution device 28 and vial 30, as illustrated by FIG. 4, and subsequent removal (or opening) of plug 58, as illustrated by FIG. 5, the reconstituted solution may then flow from vial 30 to IV bag 202 via first fluid pathway 56. Consequently, as illustrated in FIG. 7, IV fluid from IV bag 202 mixed with reconstituted solution may both be delivered, from the IV bag 202, into delivery tube 208. IV fluid from the IV bag 202 and the reconstituted drug solution may then flow to patient 206 via IV location 210. In various embodiments, flow to the IV location 210 is conveyed via gravity and/or via infusion pump 212.

The fluid conveyance process described above may, in certain embodiments, include additional steps. For example, the reconstitution device 28 may engage drug vial 30 at the cylindrical collar 48; however, prior to this engagement, the delivery tube 208 may be clamped via a typical medical line clamp. The medical professional may do this to initially ensure that any inline air (e.g., in delivery tube 208 or in reconstitution device 28) is removed from the system 200, such as by tapping the reconstitution device 28 and/or tube 208.

The above described reconstitution device, system, and method may be used, for example, during a parenteral nutrition therapy. Here, reconstitution may be used to enhance the administration of a multivitamin product that would otherwise be added to a total parenteral nutrition ("TPN") bag through the medication port. Examples of known parenteral nutrition products, which could be used with the present device, system, and method, include Olimel®, Oliclinomel, Clinomel, Clinimix®, Numeta®, ClinOleic®, SmofKabiven®, Kabiven®, PeriKabiven®, StructoKabiven, Aminomix, Nutriflex, Nutriflex Lipid, Pediaven products, and the like. In various examples, the reconstitution device 28 may be permanently connected to a TPN or multi-chamber bag 10, or may be added to the TPN or multi-chamber bag 10 prior to use.

As used in this specification, including the claims, the term "and/or" is a conjunction that is either inclusive or exclusive. Accordingly, the term "and/or" either signifies the presence of two or more things in a group or signifies that one selection may be made from a group of alternatives.

Without further elaboration, it is believed that one skilled in the art can use the preceding description to utilize the claimed inventions to their fullest extent. The examples and embodiments disclosed herein are to be construed as merely illustrative and not a limitation of the scope of the present disclosure in any way. It will be apparent to those having skill in the art that changes may be made to the details of the above-described embodiments without departing from the underlying principles discussed. In other words, various modifications and improvements of the embodiments specifically disclosed in the description above are within the scope of the appended claims. For example, any suitable combination of features of the various embodiments described is contemplated. Note that elements recited in means-plus-function format are intended to be construed in accordance with 35 U.S.C. § 112 ¶6. The scope of the invention is therefore defined by the following claims.

The invention is claimed as follows:

1. A drug reconstitution method comprising:
    enabling engagement of a first piercing member with a fluid container;
    enabling engagement of a second piercing member with a drug vial, such that intravenous ("IV") fluid may flow along a first fluid pathway formed within and extending from the fluid container to the drug vial;
    enabling mixing of the IV fluid with an agent located within the drug vial to form a mixed drug; and
    enabling removal of a removable plug, such that air from an external environment may flow along a second fluid pathway formed within and extending from the external environment to the drug vial,
    wherein air pressure in the external environment causes air to (i) flow into the drug vial via the second fluid pathway, and (ii) push the mixed drug from the drug vial to the fluid container via the first fluid pathway.

2. The drug reconstitution method of claim 1, which includes providing a reconstitution device comprising a body, the first piercing member located at a first end of its body, a collar configured to engage the drug vial, the second piercing member disposed within the collar, the first fluid pathway formed within and extending from the first piercing member to the second piercing member, and the second fluid pathway formed within and extending from the second piercing member to a portion of the body between the first piercing member and the second piercing member.

3. The drug reconstitution method of claim 2, which includes forming the removable plug fitted within the second fluid pathway at a portion of the body between the first piercing member and the second piercing member in the reconstitution device.

4. The drug reconstitution method of claim 1, which includes the removable plug forming a hermetic seal with a portion of the body between the first piercing member and the second piercing member.

5. The drug reconstitution method of claim 1, which includes initially sealing the drug vial under a vacuum.

6. A method of providing a mixed drug to a patient, the method comprising:
    providing a reconstitution device comprising
        a body,
        a first piercing member located at a first end of the body,
        a collar configured to engage a vial, and
        a second piercing member, wherein the second piercing member is disposed within the collar,
        a first fluid pathway formed within and extending from the first piercing member to the second piercing member,
        a second fluid pathway formed within and extending from the second piercing member to a portion of the body between the first piercing member and the second piercing member, and
        a removable plug fitted within the second fluid pathway at a portion of the body between the first piercing member and the second piercing member;
    enabling engagement of the first piercing member of the reconstitution device with a fluid container;
    enabling engagement of the second piercing member of the reconstitution device with a drug vial, such that intravenous ("IV") fluid may flow along the first fluid pathway formed within and extending from the fluid container to the drug vial;
    enabling mixing of the IV fluid with the drug located within the drug vial to form the mixed drug;
    enabling removal of the removable plug, such that air from an external environment may flow along the second fluid pathway formed within and extending from the external environment to the drug vial; and
    enabling the mixed drug to be provided the patient, wherein air pressure in the external environment causes air to (i) flow into the drug vial via the second fluid pathway, and (ii) push the mixed drug from the drug vial to the fluid container via the first fluid pathway.

7. The method of claim 6, which includes forming a cap integrally with the collar.

8. The method of claim 6, wherein the collar concentrically engages the vial.

9. The method of claim 6, which includes engaging the collar with the vial such that the second piercing member extends into the vial, and such that the second piercing member is placed in fluid communication with the vial.

10. The method of claim 6, which includes enabling the first piercing member to pierce an intravenous ("IV") bag port, such that the first piercing member is placed in fluid communication with the IV bag port.

11. The method of claim 6, which includes enabling the second fluid pathway to form a vent conduit.

12. The method of claim 6, which includes the removable plug forming a hermetic seal with a portion of the body between the first piercing member and the second piercing member.

13. The method of claim 6, which includes initially sealing the vial under a vacuum.

14. A method of providing a mixed drug to a patient, the method comprising:
    providing a reconstitution system comprising:
        a drug vial;
        a fluid container; and
        a reconstitution device, the reconstitution device including
            a body;
            a first piercing member located at a first end of the body;

a collar configured to engage the drug vial, and
a second piercing member, wherein the second piercing member is disposed within the collar;
a first fluid pathway formed within and extending from the first piercing member to the second piercing member;
a second fluid pathway formed within and extending from the second piercing member to a portion of the body between the first piercing member and the second piercing member; and
a removable plug fitted within the second fluid pathway at the portion of the body between the first piercing member and the second piercing member;
enabling engagement of the first piercing member of the reconstitution device with the fluid container;
enabling engagement of the second piercing member of the reconstitution device with the drug vial, such that intravenous ("IV") fluid may flow along the first fluid pathway formed within and extending from the fluid container to the drug vial;
enabling mixing of the IV fluid with the drug located within the drug vial to form the mixed drug;
enabling removal of the removable plug, such that air from an external environment may flow along the second fluid pathway formed within and extending from the external environment to the drug vial; and
enabling the mixed drug to be provided to the patient, wherein air pressure in the external environment causes air to (i) flow into the drug vial via the second fluid pathway, and (ii) push the mixed drug from the drug vial to the fluid container via the first fluid pathway.

15. The method of claim 14, which includes extending the first piercing member into the fluid container, and wherein the collar engages the drug vial such that the second piercing member extends into the drug vial, and such that the fluid container is placed in fluid communication with the drug vial via the first fluid pathway.

16. The method of claim 14, wherein the drug vial contains one of a pharmaceutical agent or a nutritional supplement.

17. The method of claim 14, which includes initially sealing the drug vial under a vacuum.

18. The method of claim 14, which includes forming the drug vial from an ultraviolet ("UV") light blocking material.

19. The method of claim 14, which includes positioning an intravenous ("IV") line to deliver a fluid from the fluid container to a patient.

20. The method of claim 19, which includes operably communicating an infusion pump with the IV line.

* * * * *